United States Patent [19]

Zaiger et al.

[11] Patent Number: Plant 7,320

[45] Date of Patent: Sep. 11, 1990

[54] CHERRY TREE 'CRAIG'S CRIMSON'

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 401,661

[22] Filed: Aug. 28, 1989

[51] Int. Cl.[5] ..... A01H 5/00

[52] U.S. Cl. ..... Plt./37

[58] Field of Search ..... Plt./37

*Primary Examiner*—James R. Feyrer

[57] ABSTRACT

A new and distinct variety of cherry tree with the following unique combination of outstanding features.

1. Semi-dwarf in size (10–14 feet tall at maturity).
2. Self fertile flowers.
3. Productive and regular bearer.
4. Medium to large size of fruit.
5. Fruit with good flavor and eating quality.
6. Fruit with attractive dark red skin color.
7. Semi-spreading growth habit.

1 Drawing Sheet

ORIGIN OF THE VARIETY

The herein variety of cherry tree was developed by us in the experimental orchard located at Modesto, Calif., as a seedling from a cross between Garden Bing Cherry (U.S. Plant Pat. No. 3,810) and a selected seedling from a group of open pollinated seeds originating from the cherry variety Stella (non-patented). The seeds were planted, grown and maintained under careful and close observation by us and gave many and varying characteristics. The present variety gave distinctive characteristics with respect to its semi-dwarf tree size and produced medium to large, good quality fruit was selected for asexual reproduction and ultimate introduction into the commercial trade.

ASEXUAL REPRODUCTION OF THE VARIETY

The present variety of cherry tree was asexually reproduced by budding, as preformed in the experimental orchard located at Modesto, Calif., shows that said characteristics run true to the original cherry tree and are established and transmitted through succeeding propagations.

SUMMARY OF THE VARIETY

The new and distinct variety of self fertile cherry tree is a regular and productive bearer of medium to large, firm, dark red fruit with good flavor and eating quality. The tree is further characterized by being semi-dwarf (approximately 10 to 14 feet tall at maturity) and having a semi-spreading growth habit.

BRIEF DESCRIPTION OF THE PHOTOGRAPHS

The accompanying photographs show reproductions of typical specimens of the foliage and fruit of our new semi-dwarf cherry variety, with the upper and lower surface of the leaves being illustrated and the exterior of the fruit being shown. The photographs were taken shortly after being picked at maturity, (tree ripe) and the colors are as nearly true as is reasonably possible in a color representation of this type.

DESCRIPTION OF THE VARIETY

The botanical details of our new and distinct variety of semi-dwarf cherry tree, its flowers, fruit and foliage are based on observations of the specimens grown near Modesto, Calif. with color definitions (except those in common terms) based on terminology in accordance with Reinhold Color Atlas by A. Korneruf and J. H. Wanscher.

Tree:
- *Size.*—Small, semi-dwarf. Approximately ⅓ to ½ normal size.
- *Vigorous.*—Semi-vigorous.
- *Growth.*—Semi-spreading.
- *Density.*—Dense to medium dense.
- *Productivity.*—Productive.
- *Bearer.*—Regular.

Trunk:
- *Size.*—Medium.
- *Texture.*—Medium rough.
- *Color.*—Grayish brown to brown (9-E-2) to (9-E-4).
- *Lenticels.*—Large. Medium number.

Branches:
- *Size.*—Medium stocky.
- *Texture.*—Medium rough.
- *Color.*—Grayish brown to reddish brown.
- *Lenticels.*—Medium to large. Medium number.

Leaves:
- *Size.*—Medium. Average length — 5½". Average width — 2".
- *Form.*—Ovate to obovate.
- *Thickness.*—Medium.
- *Margin.*—Serrate.
- *Petiole.*—Average length — 1¼". Average width — 5/64".
- *Glands.*—Range 1 to 3. Average number 2. Reniform. Primarily on upper portion of petiole.
- *Color.*—Upper surface — green to dark green (27-E-7) to (27-F-8). Lower surface — grayish green to deep green (28-D-7) to (28-E-8).

Flower buds:
- *Size.*—Large.
- *Length.*—Medium.
- *Form.*—Plump.

Flowers:
- *Blooming period.*—Mar. 18, 1989 to Mar. 24, 1989. Varies slightly due to climatic conditions.
- *Size.*—Large.
- *Color.*—White.

*Pollen.*—Present.

Fruit:

*Maturity when described.*—Tree ripe.

*Date of first picking.*—June 6, 1989.

*Date of last picking.*—June 13, 1989.

*Size.*—Medium to large. Average diameter axially — $\frac{3}{4}''$. Average transversely in suture plane — $\frac{7}{8}''$.

*Form.*—Relatively uniform. Globose to slightly oblate.

*Suture.*—Relatively smooth, some fruit slightly lipped near stem end.

*Cavity.*—Circular — shallow. Average depth — $\frac{1}{8}''$. Average width — $\frac{1}{4}''$.

*Base.*—Usually flat to slightly rounded

*Apex.*—Rounded, nearly smooth.

Skin:

*Thickness.*—Medium.

*Texture.*—Medium.

*Down.*—Wanting.

*Color.*—Red to dark red — (10-B-8) to (10-D-8).

*Tendency to crack.*—None during dry weather. Slight during wet weather.

Flesh:

*Texture.*—Firm.

*Ripens.*—Relatively even.

*Flavor.*—Subacid, mild.

*Juice.*—Moderate.

*Eating quality.*—Good.

*Color of flesh.*—Light pink to red.

Stone:

*Type.*—Semi-freestone.

*Size.*—Medium. Average length — 11/32". Average breadth — $\frac{3}{8}''$. Average thickness — $\frac{1}{4}$.

*Form.*—Oblong.

*Tendency to split.*—None.

*Color.*—Light brown — (6-B-4) to (6-B-5).

Stem of fruit:

*Size.*—Average length — $1\frac{1}{4}''$. Average width — 3/32".

Use: Dessert. Local and long distance markets.

Keeping quality: Good.

Shipping quality: Good.

The semi-dwarf cherry tree, its foliage and fruit herein described may vary in slight detail due to climatic, soil conditions and cultural practices under which the variety may be grown; the present description is that of the variety grown under the ecological conditions prevailing at Modesto, Calif.

We claim:

1. A new and distinct variety of cherry tree, substantially as illustrated and described, characterized by its semi-dwarf size, 10 to 14 feet at maturity, its semi-spreading growth, self fertility and being a regular and productive bearer of medium to large size fruit with an attractive dark red skin color and having good flavor and eating quality.

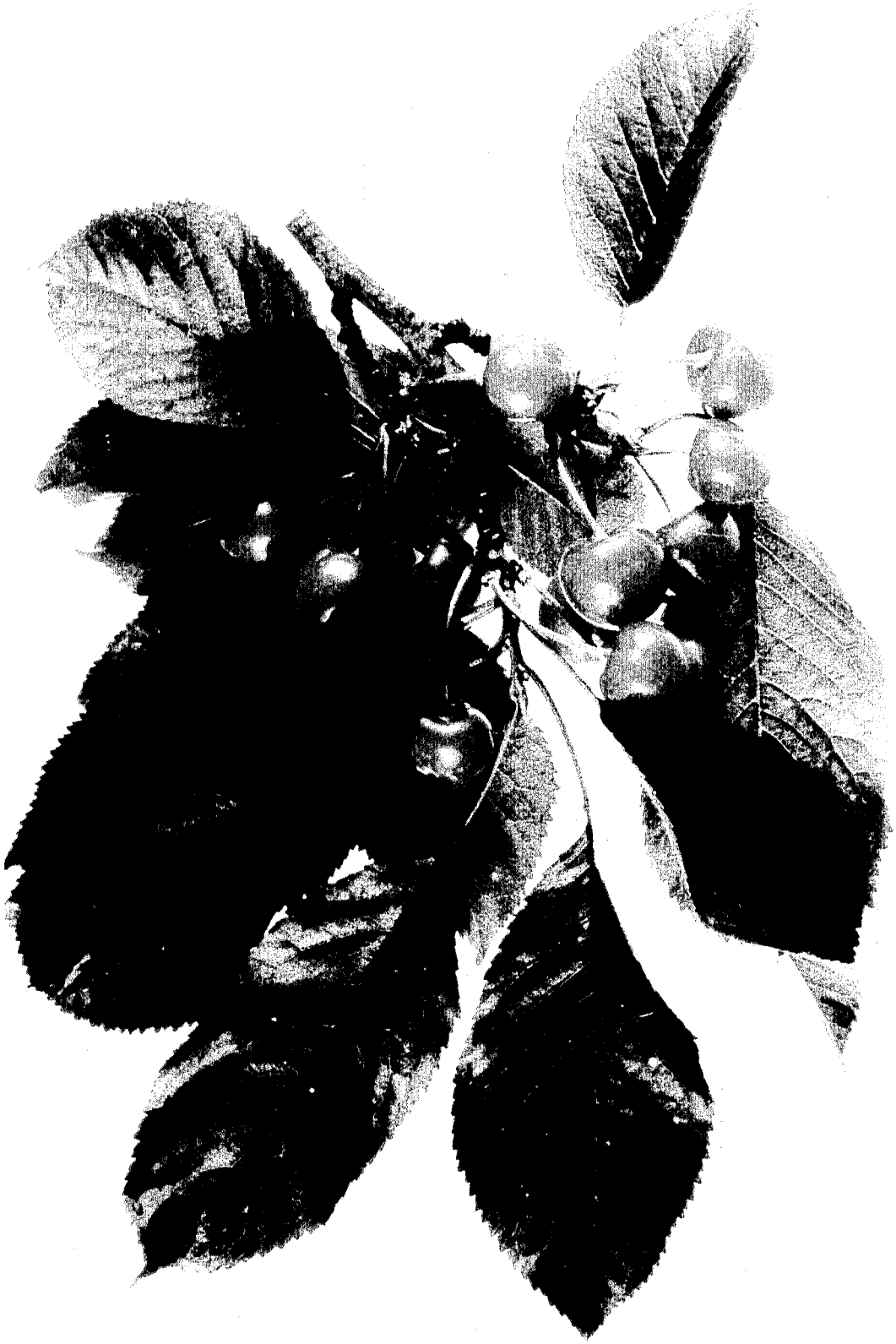

* * * * *